US008287474B1

(12) United States Patent
Koenig et al.

(10) Patent No.: US 8,287,474 B1
(45) Date of Patent: Oct. 16, 2012

(54) METHOD AND APPARATUS FOR NONINVASIVELY INCREASING WHOLE BODY BLOOD FLOW AND NONINVASIVE PHYSICAL EXERCISE OF LIMBS FROM THE OUTSIDE AND FROM WITHIN THE LIMB TO TREAT DISEASES THROUGHOUT THE BODY

(76) Inventors: J. Frank Koenig, Vienna, VA (US); John J. Basile, Potomac, MD (US)

( * ) Notice: Subject to any disclaimer, the term of this patent is extended or adjusted under 35 U.S.C. 154(b) by 0 days.

(21) Appl. No.: 12/385,419

(22) Filed: Apr. 7, 2009

Related U.S. Application Data

(63) Continuation-in-part of application No. 11/415,420, filed on May 2, 2006, now Pat. No. 7,513,879, and a continuation of application No. 10/645,869, filed on Aug. 22, 2003, now Pat. No. 7,037,257.

(60) Provisional application No. 60/404,933, filed on Aug. 22, 2002.

(51) Int. Cl.
 *A61H 7/00* (2006.01)
 *A61H 19/00* (2006.01)
(52) U.S. Cl. ............... 601/9; 601/6; 601/152; 601/151; 601/149; 601/148
(58) Field of Classification Search ............... 601/6–14, 601/5, 23, 25, 148–152; 128/202.12, 203.13, 128/205.26, 898, DIG. 20; 482/54; 600/19, 600/21, 22, 38
See application file for complete search history.

(56) References Cited

U.S. PATENT DOCUMENTS

| 2,055,128 | A | * | 9/1936 | Herrmann | 601/9 |
|---|---|---|---|---|---|
| 2,235,138 | A | * | 3/1941 | Billetter | 601/9 |
| 3,094,983 | A | * | 6/1963 | MacLeod | 601/9 |
| 3,403,673 | A | * | 10/1968 | MacLeod | 601/9 |
| 3,465,748 | A | * | 9/1969 | Kravchenko | 601/6 |
| 3,859,989 | A | * | 1/1975 | Spielberg | 601/11 |
| 4,738,249 | A |  | 4/1988 | Linman et al. |  |
| 5,000,164 | A | * | 3/1991 | Cooper | 601/11 |
| 5,133,339 | A | * | 7/1992 | Whalen et al. | 601/23 |
| 5,356,361 | A | * | 10/1994 | Watenpaugh | 482/111 |
| 6,183,414 | B1 |  | 2/2001 | Wysor et al. |  |
| 6,376,554 | B1 |  | 4/2002 | Cheetham et al. |  |
| 6,398,720 | B1 |  | 6/2002 | Dabal |  |
| 6,414,027 | B1 |  | 7/2002 | Neal |  |
| 6,436,944 | B1 |  | 8/2002 | Maytom |  |

(Continued)

OTHER PUBLICATIONS

J. Chen et al. "Combining Intracavernous Injection and External Vacuum as Treatment for Erectile Dysfunction", May 1995, Journal of Urology, vol. 153, issue 5, pp. 1476-1477, copyright 1995.

(Continued)

*Primary Examiner* — Annette Dixon
(74) *Attorney, Agent, or Firm* — Shlesinger, Arkwright & Garvey LLP

(57) ABSTRACT

A noninvasive treatment to increase the elasticities of arteries and veins in arms, legs, hands and feet, to reduce heart workload, to increase whole body blood flow, to supply an increased amount of oxygen and nutrients throughout the cardiovascular system and increase the rate of removal of cell waste products, to treat many medical conditions so that symptoms are eliminated or minimized due to improved performance of the body. The noninvasive treatment includes using a vacuum pressure and air pressure system to perform the above, and to passively exercise muscles of arms, legs, hands and feet in a chamber, and is suited for patients who are unable to engage in sufficient exercise on their own.

2 Claims, 2 Drawing Sheets

U.S. PATENT DOCUMENTS

| | | |
|---|---|---|
| 6,548,544 B1 | 4/2003 | Adaikan et al. |
| 6,589,990 B1 | 7/2003 | Kanakaris et al. |
| 7,037,257 B1 | 5/2006 | Koenig et al. |
| 7,405,222 B2 | 7/2008 | Sallis et al. |

OTHER PUBLICATIONS

J. Chen et al. "Concomitant Use of Sildenafil and a Vacuum Entrapment Device for the Treatment of Erectile Dysfunction", Jan. 2004, Journal of Urology, vol. 171, pp. 292-295, copyright 2004.

Kiefer, Dale, "Doctors Ignore Proven Alternative to Coronary Stents and Bypass Surgery", *Life Extension*, Jun. 2008 pp. 53-60.

Braverman, Debra, *Heal Your Heart with EECP*, publisher Celestial Arts, Berkely, Calif., 2005 Title page, front is page with publication information, ISBN-13:978-1-58761-244-2 (2 pgs.).

San Francisco Heart Institute at Seton Medical Center, http://www.sfhi.com/trmtoptions.htm#MinimallyInvasiveBypassSurgery (MIDCAB), dated Apr. 28, 2009 (pp. 8-10 of 12) (3 pgs.).

\* cited by examiner

METHOD AND APPARATUS FOR NONINVASIVELY INCREASING WHOLE BODY BLOOD FLOW AND NONINVASIVE PHYSICAL EXERCISE OF LIMBS FROM THE OUTSIDE AND FROM WITHIN THE LIMB TO TREAT DISEASES THROUGHOUT THE BODY

CROSS-REFERENCE TO RELATED APPLICATIONS

This application is a continuation-in-part of application Ser. No. 11/415,420, filed May 2, 2006, now U.S. Pat. No. 7,513,879, issued Apr. 7, 2009, is a continuation of application Ser. No. 10/645,869, filed Aug. 22, 2003, now U.S. Pat. No. 7,037,257, issued May 2, 2006, which claims the priority of 60/404,933, filed Aug. 22, 2002, and each of which is incorporated herein by reference.

This application relates to the following four (4) disclosure documents, each of which incorporated herein by reference:
1. Disclosure Document No. 510,869, filed May 6, 2002;
2. Disclosure Document No. 507,608, filed Mar. 19, 2002;
3. Disclosure Document No. 505,659, filed Feb. 20, 2002; and
4. Disclosure Document No. 499,108, filed Aug. 29, 2001.

Each of these four disclosure documents was filed with applicant's application Ser. No. 10/645,869, filed Aug. 22, 2003, now U.S. Pat. No. 7,037,257, issued May 2, 2006.

FIELD OF THE INVENTION

The inventive apparatus and method applies to the treating of the cardiovascular system and the whole body to increase whole body blood flow by increasing the elasticity of veins and arteries to treat many conditions. The invention also includes a vacuum-air apparatus and method for passive physical exercise of limbs from the outside and also from the inside of each limb by cycling artery and vein blood pressure, to dilate and relax these blood vessels, to exercise surrounding muscle.

BACKGROUND OF THE INVENTION

U.S. Pat. No. 6,183,414 to Wysor et al. uses a periodic vacuum pump noninvasive treatment to overcome erectile dysfunction so that after a number of treatment sessions, the patient has a natural, normal sex. Additional vacuum treatment is eventually required to maintain normal erectile function, without medications.

U.S. Pat. No. 4,738,249 to Linman et al. describes a method and apparatus for enhancing blood circulation in a predetermined portion of a patient's body, remote from the patient's heart, by distending (dilating) and relaxing arteries and veins in a vacuum chamber. Linman '249 differs from the present invention as will be described in greater detail below.

Enhanced External Counterpulsation (EECP) is described in a 2005 book, *Heal Your Heart with EECP*, by Dr. Debra Braverman, MD. The EECP treatment program, using cuff squeezing of legs, covers 7 weeks, causes the whole body blood flow to gradually increase so that after the 7 weeks the blood flow remains high for up to 5 years. This high blood flow provides an increased amount of oxygen and nutrients to the whole body to treat a large number of medical conditions. EECP also provides physical exercise to the muscles of each leg by squeezing.

EECP has been found effective in over 100 studies. Braverman lists medical conditions for which there is evidence of EECP effectiveness, including dementia, chronic stable angina, cardiogenic shock, congestive heart failure, during a heart attack, arthritis, atherosclerosis, heart disease, heart attack, stroke, diabetes, cardiomyopathy, cardiovascular disease, heart failure, diabetic retinopathy, chronic leg ulcers, chronic wounds, peripheral neuropathy, peripheral vascular disease, restless leg syndrome, shortness of breath, deficient sleep patterns, visual disorders, deficient thought clarity, coronary artery disease, deep vein thrombosis, depression, erectile dysfunction, athletic performance, rheumatoid arthritis, chronic infections, deficient eye blood flow, nerve injury, Parkinson's disease, hearing disorders, and tinnitus.

The known Enhanced External Counterpulsation (EECP) treatment, which is a noninvasive treatment to reduce heart workload and increase blood flow throughout the body to provide an increased amount of oxygen and nutrients to the cells and provide an increased rate of removal of cell waste products. EECP is approved by the U.S. Food and Drug Administration for chronic stable angina, cardiogenic shock, congestive heart failure, as well as during a heart attack. It is also effective in the treatment of other conditions throughout the body. EECP is described in a 2005 book, *Heal Your Heart with EECP* by Dr. Debra Braverman, M.D. Symptoms are eliminated or minimized for up to five years, due to increased blood flow throughout this time period. The treatment is painless and there are no adverse effects. EECP also provides passive exercise for ambulatory and non-ambulatory patients. Typically the treatment comprises thirty-five one hour sessions, one hour/day, five days/week for seven weeks.

For that Braverman EECP treatment, the patient lies on a special bed, and a therapist wraps a set of oversized blood pressure cuffs tightly around the patient's calves, lower thighs and upper thighs. An air hose connects each cuff to an air compressor. Each cuff inflates (squeezes) with air for 50 milliseconds (ms), sequentially: first the calves, then the lower thighs, then the upper thighs, and then all cuffs deflate simultaneously. It is common practice in the United States to place the known cuffs only on the legs rather than on arms and legs.

The trigger for the cuffs to inflate and deflate is the patient's heartbeat. With three stick-on electrodes on the patient's chest, a computer reads the patient's EKG (electrocardiogram) continuously throughout the treatment and uses it to synchronize the inflation and deflation of the cuffs to the patient's heart beats. When the patient's heart beats, all cuffs deflate and the heart supplies blood to the legs. When the heart rests, between beats, the cuffs inflate in sequence and squeeze the patient's legs so that blood is forced upward in the leg arteries and veins towards the heart.

This analysis of EECP is by the present inventors.

The squeezing by the three cuffs moves blood upward in the leg arteries, which causes momentary arterial dilation for two reasons. The first reason is because the closed aortic valve, during the rest period, prevents arterial blood from back-flowing into the heart, so that the blood squeezed upward by the cuffs momentarily dilates leg arteries. The second reason is that due to friction between the blood and arterial walls, the blood flow is slowed (opposed) so that momentary arterial dilation will occur above each cuff, as each cuff squeezes the arteries. It will be shown by the present inventors that arterial elasticities are increased.

When blood is forced upward in the veins, the flow is slowed (opposed) by the friction between the blood and the walls, resulting in momentary dilation of the veins. It will be shown by the present inventors that venous elasticities are increased.

During squeezing by any cuff, the blood that is forced upward will also dilate the arteries and veins located underneath the cuff. This dilation increases the elasticities of these arteries and veins. For the lower thigh cuff or upper thigh cuff, when each cuff is squeezed, sequentially, blood is blocked from moving downward by the inflated cuff below. Blood moves upward, underneath the inflated cuff, and momentarily dilates the arteries and veins under the cuff before flowing above the cuff to dilate arteries and veins, to increase vessel elasticities.

When the calf cuff inflates, blood flow at the lower end of the calf cuff is not blocked because there is not an inflated cuff below the calf cuff, so that extra blood will be forced into the arteries and veins of the foot, to increase the elasticities of these vessels. Simultaneously, blood will be forced upward, underneath the cuff, to dilate vessels underneath the cuff and vessels above the cuff, to increase vessel elasticities.

According to the present inventors, the primary reasons why EECP is effective in increasing blood flow everywhere in the body, during and after each EECP treatment session, can be explained by a finding of the present inventors, such as described in our U.S. Pat. No. 7,037,257 to Koenig et al., issued May 2, 2006, the entirety of which is and has been incorporated herein by reference.

The Wysor et al. '414 patent states that their method and apparatus treats erectile dysfunction when this condition is due to insufficient plasticity of the penile tissues. The present inventors found that Wysor's periodic vacuum pump treatment for erectile dysfunction is effective because it gradually increases the elasticity of penile arteries and veins, rather than increasing the plasticity of penile tissue, as stated in Wysor '414.

OBJECTS AND SUMMARY OF THE INVENTION

It is an object of the invention to overcome the drawbacks of the prior art.

To assist in understanding the objects and summary of the invention, comparison with earlier treatments by others will likewise be set forth herein.

The finding of the present inventors states: Forceful dilation of arteries and veins, by momentarily increasing blood pressure, will cause an immediate and temporary increase in arterial and venous elasticities. This finding applies to all arteries and veins in the body because all vessels have the same wall design, comprising the same three layers.

Another aspect of the method according to the present invention is that the vacuum air method is not limited to use on penile arteries and veins but applies to all of the arteries and veins in the body because all arteries and veins in the body are of the same common physical design, with the same three layers.

The inventive method and apparatus achieves: periodic forceful dilation of arteries and veins, anywhere in the body, which causes a gradual increase in the elasticities of these arteries and veins.

During a heart attack, EECP aids the weakened heart by forcefully assisting the return of venous blood to the heart. According to the present inventors, EECP reduces heart workload by immediately increasing the elasticities of arteries and veins in the legs. By immediately reducing heart workload, EECP immediately increases blood flow into the heart and throughout the body, to immediately increase the amount of oxygen and nutrients into the heart and throughout the body, while increasing the rate of removal of cell waste products.

The finding by the present inventors explains why EECP is immediately effective, e.g. during a heart attack. The inventive method, and finding, explains why the periodic EECP treatment sessions gradually increase blood flow throughout the body so that after completion of all sessions the blood flow will remain high and effective for up to five years.

The following is a comparison of the known EECP treatment and the Wysor '414 treatment.

Both treatments are noninvasive and have no adverse effects. EECP is applied to the legs while the Wysor '414 treatment is applied to the penis. EECP gradually increases the elasticities of the arteries and veins in the legs and feet. The Wysor '414 treatment gradually increases the elasticities of the arteries and veins in the penis. EECP usually requires 1 session/day, 5 sessions/week, 35 sessions over 7 weeks. The Wysor '414 treatment usually requires 1 session/day, 5 sessions/week, for up to several months. After completing EECP, patients will have no or minimal symptoms for up to five years.

After completing the known Wysor treatment, patients will have normal, natural sex, without medications. The EECP and Wysor patients will eventually require additional treatment because the elasticities will gradually decrease over time.

Arteries, with or without plaque, veins and muscles, become less flexible (elastic) throughout life. Concerning exercise, as the patient relaxes in the special bed, EECP provides passive exercise for both ambulatory and non-ambulatory patients. The cuff squeezing of leg muscles provide passive exercise. In addition, according to the present inventors, the forceful dilation of arteries and veins exercises the muscles surrounding these vessels, so that these muscles, in addition to arteries and veins, become more flexible (elastic). The finding by the present inventors can be expanded to state: Forceful dilation of arteries and veins causes an increase in the elasticities of these arteries, veins and surrounding muscle. Later a passive exercise apparatus will be described.

EECP scientists found that EECP increases blood flow throughout the body. This finding shows that EECP reduced the heart workload, to increase blood flow. The present inventors showed that the reduction in workload is due to an increase in vessel elasticities in legs. EECP does not flatten arterial plaque, which reduces blood flow in all arteries in which plaque is present. Arterial plaque increases heart workload because it partially blocks arteries. This further suggests that the flattening of arterial plaque located anywhere in the body, will increase blood flow throughout the body. This further suggests that if EECP is used in combination with balloon or noninvasive vacuum angioplasty, the increase in blood flow throughout the body may by greater than for each treatment used separately.

Our inventive vacuum therapy method and apparatus work better than each of the above.

Our apparatus (vacuum pressure and air pressure in a chamber) in accordance with the invention is versatile. It is used for:

(1) exercising arms, legs, hands and feet, or a portion thereof, by applying a cyclic uniform air pressure to any or all of these body parts, during the air pressure mode of operation; during the vacuum mode of operation, a cyclic vacuum pressure is applied uniformly to any, or all, or a portion of these body parts to cyclically dilate the arteries and veins by cycling the blood pressure to cyclically dilate and exercise surrounding muscles;

(2) Increasing artery and vein elasticities, in a vacuum, by momentarily increasing blood pressure (momentary vacuum therapy) to dilate arteries and veins, to reduce heart workload and increase whole body blood flow to eliminate or minimize symptoms due to improved body performance;

(3) Application of our noninvasive vacuum angioplasty procedure in combination with our procedure to increase the elasticities of arteries and veins in the limbs, to attain a higher level of whole body blood flow than for either procedure used separately; and (4) In vacuum, periodic dilation of arteries and veins, to gradually increase whole body blood flow, so that the blood flow remains high after a number of sessions to treat many conditions, without medications.

Our treatment may be more effective than EECP because we can maximize vessel elasticities to maximize whole body blood flow to eliminate or minimize symptoms because of improved body performance.

Additional Advantages Include:

Unlike the present invention, the known EECP apparatus is a dynamic machine, with performance synchronized to the patient's heart beat. Each known cuff squeezes the legs for a typical synchronized 70 times/minute, which makes it unsuitable for the treatment of some patients. EECP is contraindicated for severe peripheral vascular diseases, decompensated congestive heart failure, uncontrolled hypertension, phlebitis, deep vein thrombosis, pregnant or potentially pregnant women, significant aortic insufficiency, and markedly irregular heart rhythm.

The invention of the present inventors includes the advantage that the apparatus does not require synchronization to the heart beat.

Also, the vacuum-air exercise machine of the present invention, which increases vessel elasticities, can cycle the air pressure and vacuum as slowly or swiftly as needed for the patient's condition. Further, that can be done for any number of cycles per minute and with any air pressure, applied externally, and any internal vessel pressure applied to surrounding muscle within the limbs. Exercise in accordance with the invention is achieved 100 percent of the time rather than 6 percent of the time per the prior art EECP cuff, applied to only about one-third of the leg length. The apparatus according to the present invention may reduce heart workload a greater amount than EECP, while also being suitable for some patients for which EECP is contraindicated.

Braverman's book provides images of the heart showing the growth of new blood vessels due to EECP. This vessel growth, called angiogenesis, helps to alleviate coronary artery disease by rerouting blood flow around clogged arteries so it can reach the heart. The exercise machine of the present invention may also promote angiogenesis, because increased blood flow stimulates angiogenesis.

The inventive apparatus and method includes alternating the application of negative air pressure and positive air pressure, as well as alternating the application of negative pressure and ambient air pressure. For convenience this may likewise be referred as alternating vacuum pressure and air pressure or vacuum-air method according to the invention.

The invention likewise includes a method of increasing the elasticity of arteries and veins of a portion of a patient's body remote from the heart, the method including providing a chamber, the chamber being configured for receiving a portion of a patient's body that is remote from the heart, the chamber being pressurizable and depressurizable. Providing a vacuum source, the vacuum source being configured for inducing a negative pressure in the vacuum chamber. Locating a portion of a patient's body in the vacuum chamber, causing the vacuum source to induce a negative pressure on the portion of the patient's body remote from the patient's heart, and causing the vacuum source to relieve the negative pressure to return the pressure in the chamber to ambient pressure after a predetermined period of time, inducing and relieving the negative pressure a sufficient number of times to increase the elasticity of the arteries and veins of the portion of the patient's body located in the vacuum chamber, and inducing and relieving the negative pressure independent of the patient's heartbeat.

The invention further includes that the portion of the patient's body remote from the patient's heart includes substantially the patient's entire leg, and the portion of the patient's body remote from the patient's heart includes all or a part of the patient's leg or arm, for example. The part of the patient's leg includes from above a knee to above an ankle of the patient's leg, for example, or from below the knee to the entire foot of the patient's leg, or from above a knee to an upper portion of the thigh of the patient's leg.

The invention further includes the inducing and relieving of the negative pressure described above is performed a sufficient number of times to increase the elasticity of the arteries and veins, and to exercise the muscles adjacent the arteries and veins of the portion of the patient's body located in the vacuum chamber.

Relative terms, such as up, down, left, and right are for convenience only and are not intended to be limiting.

Atmospheric pressure may be also referred to as ambient pressure.

Negative pressure refers to a pressure below atmospheric pressure, and may also be referred to as a vacuum.

Positive pressure refers to a pressure greater than atmospheric pressure.

DETAILED DESCRIPTION OF THE INVENTION

It should be noted that the present inventors are the inventors of the parent application Ser. No. 11/415,420, filed May 2, 2006, now U.S. Pat. No. 7,513,879 to Koenig et al., issued Apr. 7, 2009, which discloses a method and apparatus for noninvasive vacuum angioplasty that can be used to flatten arterial plaque in arms, legs, hands and feet.

Figure 1:
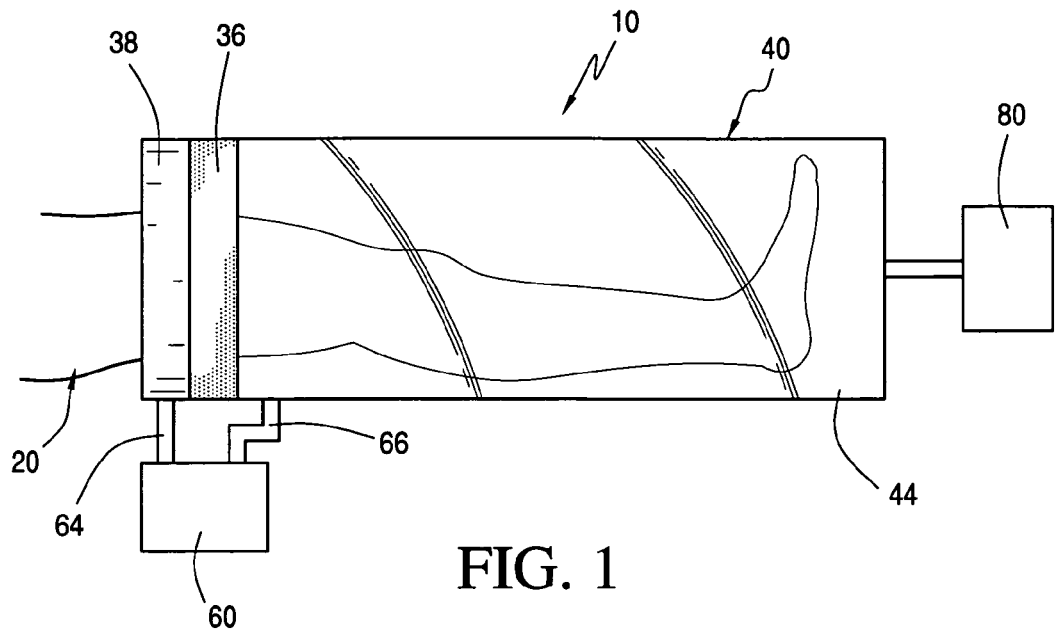
FIG. 1 shows the inventive method and apparatus in use for treating an entire leg.

FIG. 1 of the present invention shows a first embodiment of an apparatus 10 according to the invention, applied to a whole leg 20. An elastomeric sleeve 36 connects a vacuum chamber 40 to a pneumatic cuff 38. The cuff 38 seals the chamber 40 to the leg 20. A case 44 of chamber 40 may be, e.g. plastic, transparent and cylindrical for ease of viewing by the medical personnel treating the leg 20 of a patient, in use. An air compressor 60 is connected to the pneumatic cuff 38 by a pressure line 64. A vacuum pump 80 is connected to the chamber 40. The cuff pressure is adjusted high enough to provide a vacuum seal, without interfering with blood flow. To flatten plaque, the vacuum pressure is adjusted so that the arterial pressure, inside the chamber 40, is the same plaque-flattening pressure that is applied to plaque by the balloon in balloon angioplasty. As used in a well known prior art hand vacuum pump for erectile dysfunction, the arterial blood pressure, inside the chamber, is the sum of the systolic arterial pressure, outside the chamber, plus the absolute value of the vacuum pressure inside the chamber. The cardiologist can adjust the arterial pressure, inside the chamber, in order to flatten plaque. The same monitoring apparatus can be used as for balloon angioplasty.

In the case where the pressure inside vacuum chamber 40 must be greater than atmospheric pressure, then air in chamber 40 may be pressurized by compressor 60 thanks to an optional pressure line 66.

To flatten arterial plaque in any portion of a leg, e.g. from the upper thigh to immediately below the knee, FIG. 2, another embodiment of a vacuum chamber 140 of shorter length is used, with two elastomeric sleeves 36, 136 connected to the chamber 140 and to the two pneumatic cuffs 38, 138. The cardiologist performs the vacuum angioplasty.

Figure 2:
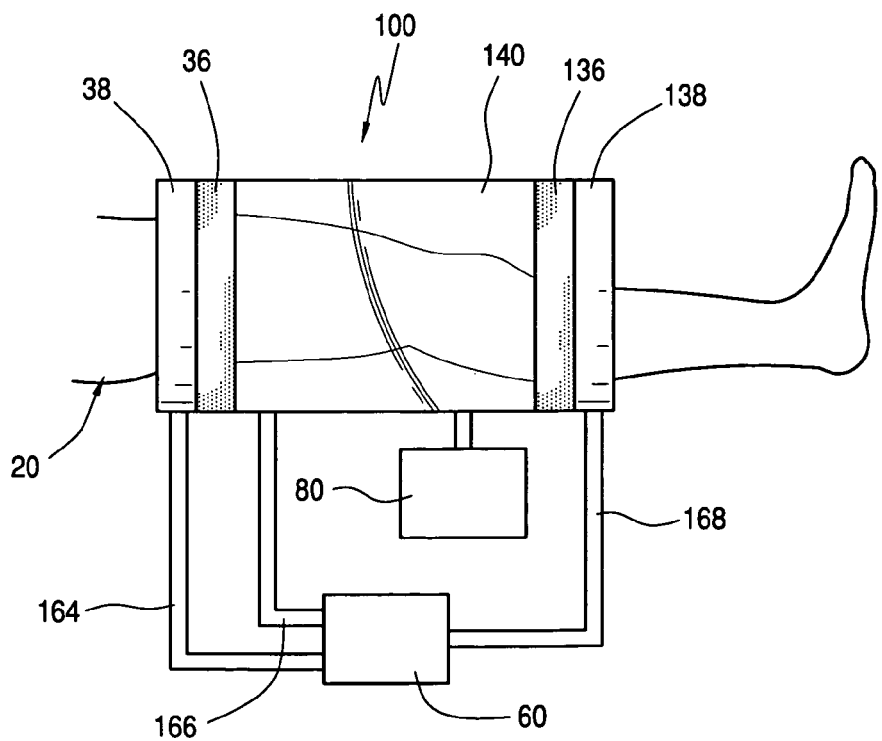
FIG. 2 shows another embodiment of the inventive apparatus applied to a portion of the leg from the thigh to below the knee of a patient.
Figure 3:
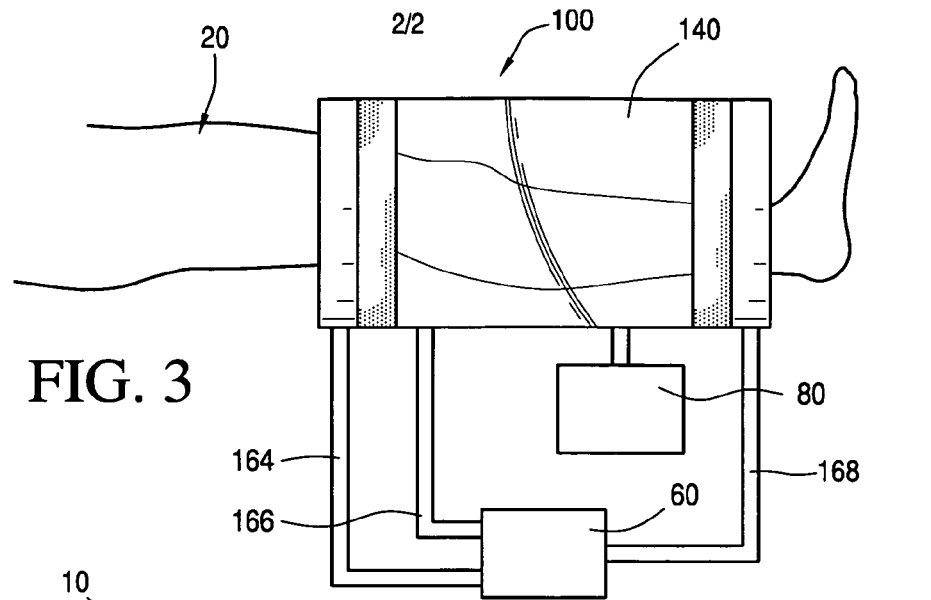
FIG. 3 shows the inventive apparatus according to the embodiment of FIG. 2 applied to a lower portion of the leg, such as the illustrated from above the knee to above the foot.
Figure 4:
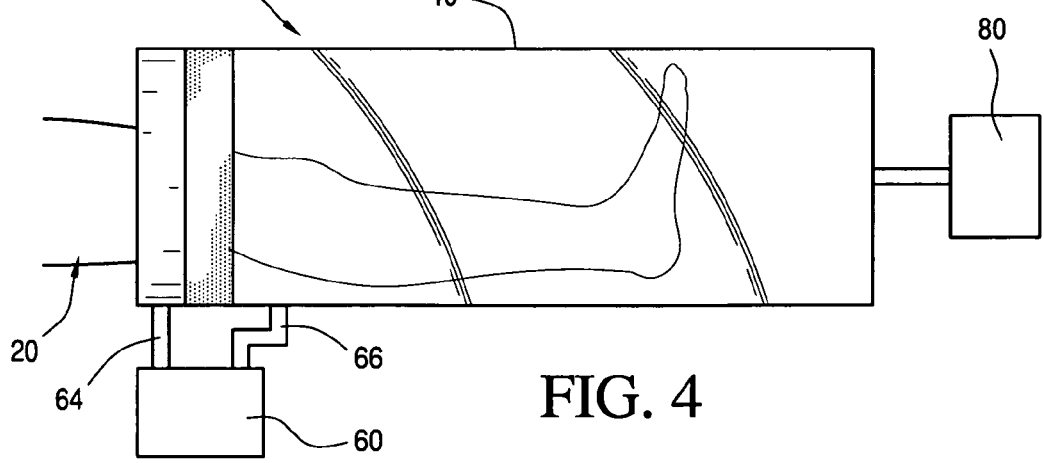
FIG. 4 shows the embodiment of FIG. 1 applied to a portion of the patient's leg, beginning from above the knee and including the patient's foot.
Figure 5:
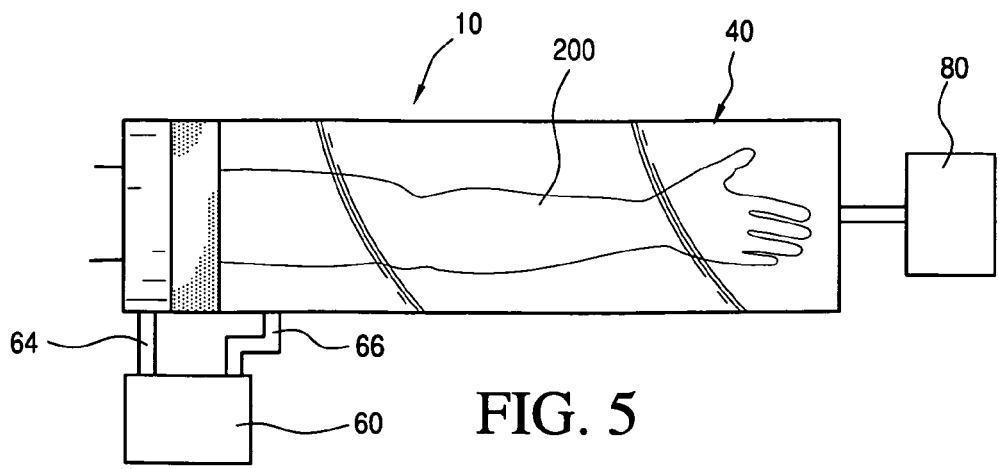
FIG. 5 shows the inventive apparatus of the embodiment of FIG. 1 being used in accordance with the method according to the invention for treating substantially an entire arm.

The apparatus 10, FIG. 1 and apparatus 100 of FIG. 2, used for noninvasive vacuum angioplasty and for increasing arterial elasticity, can also be used to dilate arteries and veins in arms, legs, hands and feet, to increase the elasticities of these vessels so that heart workload is reduced and blood flow is increased throughout the body.

Blood flow, throughout the body, can be measured by the same device used by the EECP practitioners. It is the finger plethysmographic waveform (FPW), which clips to a finger. It uses an infrared light to measure blood flow in the tiny arteries of a finger. It accurately reflects the amount of blood flow throughout the body.

The following method and apparatus is for increasing artery and vein elasticities, FIGS. 1-5. After vacuum sealing, if the cuff pressure is gradually increased, the venous blood flow will be gradually reduced until a cuff pressure is attained for which venous flow is blocked. Arterial flow is not altered into the chamber until venous flow is blocked. As the venous blood flow is gradually reduced, the venous blood pressure, in chamber, will gradually rise to the arterial pressure, in chamber, as explained later. If the vacuum pressure is gradually increased, the arterial and venous pressures, now equal inside the chamber, will gradually increase the same amount as the increase in vacuum pressure. The vacuum pressure can be cycled to dilate the arteries and veins to increase vessel elasticities. The FPW device is used to measure whole body blood flow before, during and after treatment. The cardiologist specified the maximum blood pressure to be used.

The above example was for equal arterial and venous blood pressures for which the vacuum pressure was cycled to increase the vessel elasticities. During cycling, it is necessary that the maximum blood pressure achieved, for the arteries and veins, of equal pressure, be not greater than the maximum safe pressure for the veins, because the maximum safe pressure for veins is lower than the maximum safe pressure for arteries. This is because arteries function at higher normal pressures than veins. Arterial walls are stronger than venous walls. This procedure is useful when the cardiologist wants to cycle the venous pressure any amount up to the maximum safe value of venous pressure.

If it is desired to cycle the arterial and venous pressures so that the maximum safe arterial pressure is attained without damaging the veins, this can be achieved by reducing the cuff pressure so that venous flow is normal; the cuff pressure is now only sufficient for a vacuum seal. Adjust the vacuum pressure to achieve the safe maximum arterial pressure. Cycle the vacuum pressure to cycle the arterial and venous pressures. Since there is no venous flow blockage, the maximum venous pressure, during cycling, will be below the arterial pressure. The cardiologist controls the vacuum pressure and the arterial pressure, in chamber. He uses the formula: Arterial pressure, in chamber, is the sum of the patient's systolic arterial blood pressure (monitored continuously) and the vacuum pressure (controlled by the cardiologist).

When venous flow is blocked, the venous blood pressure rises to the arterial pressure, in chamber. This rise can be explained as follows: In chamber, arterial blood flow branches into smaller arteries called arterioles, which branch into capillaries, which converge into the smaller veins called venules, which converge into the veins. Arterial blood passes through these vessels to become venous blood. When venous flow is blocked, outside chamber, arterial flow will stop because the venous blockage stops blood flow in the veins, venules, capillaries, arterioles and arteries. The heart continues to apply pressure to the arteries but no arterial blood will flow into the chamber due to the venous blockage.

The arterial blood pressure (the driving force) is transmitted undiminished through the motionless blood in the arterioles, capillaries, venules, and veins, so that the venous blood pressure is equal to the arterial blood pressure, when venous blood flow is blocked.

Earlier it was stated by the present inventors that the known EECP provides passive physical exercise in two ways. First, the cuffs squeeze the leg muscles, in sequence. Each of the three cuffs squeezes for one-third of the total cuff squeezing time during the rest period (diastole) of the heart, which comprises about two-thirds of the cardiac cycle. The heart beat (systole) comprises the other one-third. Secondly, each cuff squeeze caused dilation of arteries and veins which exercises surrounding muscle.

A typical heart rate is 70 beats/minute, which corresponds to 860 milliseconds/cardiac cycle. The rest period is 576 ms and the beat period is 284 ms for each cardiac cycle.

Each EECP cuff squeezes for 50 ms, which is only 6 percent of a cardiac cycle, and each cuff covers only about one-third of the length of the leg. There is no cuff for the foot. In contrast, the air pressure exerciser of the present inventors, as shown in FIG. 1, for example, applies a uniform pressure to the entire leg and foot. The air pressure variation can be programmed to the condition of the patient. If necessary, warm or cool air can be applied to the leg, foot, arm and hand, if needed as part of a treatment used by the cardiologist.

Concerning known EECP dilation of arteries and veins, each cuff squeezes for only 6 percent of a cardiac cycle.

In contrast to that, the vacuum system of the present invention dilates, simultaneously, all vessels of the entire leg and foot, as well as the arm and hand. Also, the vessel elasticities can be maximized, to minimize heart workload and maximize whole body blood flow.

The apparatus of FIG. 1 and FIG. 2 can provide air pressure and vacuum exercise. If the venous blood flow is blocked, outside chamber, then the arteries and veins in chamber will have the same blood pressure. If the vacuum pressure is cycled, the artery and venous pressures will cycle, by the same amount, to dilate arteries and veins, and to exercise surrounding muscle. When cycling, the vacuum pressure can be set at a value corresponding to a value of venous pressure up to the maximum safe venous pressure. An alternate procedure is to adjust the vacuum pressure for up to a maximum safe arterial pressure and adjust the cuff pressure for up to a maximum safe venous pressure, to maximize muscle dilation, for maximum safe exercise. The pressures used depend upon the patient's condition. An additional benefit for the patient is an increase in arterial and venous elasticities.

Additional passive exercise is achieved if the air compressor in FIGS. 1-5 is also connected to the chamber, as shown by the illustrated optional pressure lines 66 and 166, respectively, with the vacuum pump turned off. Air pressure can be cycled to exercise leg and foot muscles. When cycling, the maximum air pressure provided by respective compressors 80, 180 can be set for optimum exercise for the patient's condition, specified by cardiologists, vascular scientists and physical therapists. A uniform air pressure is applied to legs and feet. These professionals can specify whether arms, legs, hands and feet can be safely exercised simultaneously, using one chamber for legs and feet and another chamber for arms and hands. A computer program, e.g., can cycle the air pressure so that, e.g., early cycles have a lower maximum air pressure than later cycles. The required air pressure variation can be programmed to the condition of the patient.

Ambulatory and non-ambulatory patients and others can benefit from the air pressure passive exerciser and the vacuum pressure passive exerciser of the present invention. These exercisers are painless and have no known adverse effects. The vacuum pressure passive exerciser has the benefit of passively exercising the muscles surrounding the arteries and veins in arms, legs, hands and feet by dilating these arteries and veins to produce an additional benefit: increasing the elasticities of arteries and veins to reduce heart workload to increase whole body blood flow to provide an increased amount of oxygen and nutrients and an increased rate of removal of cell waste products to treat a wide variety of conditions throughout the body to eliminate or minimize symptoms by improving whole body performance. Periodic use of the vacuum exerciser, which also increases vessel elasticities, leads to a higher level of whole body blood flow, as shown earlier.

The vacuum pressure exerciser and the air pressure exerciser can be combined, thanks to use of respective vacuum pumps 80, 180, and respective compressor 60, 160 of FIGS. 1-5, each of which embodiments uses a common respective vacuum chamber 40, 140, with alternating vacuum pressure and air pressure. An advantage of alternating pressurizing with air compressor 60, 160 and vacuum pump 80, 180, respectively, is that venous blood is flushed from the chamber during the air pressure time period so that the risk of blood clots is minimized. The vacuum pressure time period and the air pressure time period are adjustable. The vacuum pressure variation and the air pressure variation are adjustable. For example, during an exercise session, lower vacuum and air pressures may be used at the beginning of an exercise session than later in the session. Cardiologists, vascular scientists and physical therapists can specify the vacuum and air pressure variations which are best for each patient. The method is performed without the use of an external oxygen supply for the patient's body, and no such supply is shown in the Figs.

E. K. Linman et al., U.S. Pat. No. 4,738,249, describe a method and apparatus for enhancing blood circulation in a predetermined portion of a patient's body, remote from the patient's heart, by distending (dilating) and relaxing arteries and veins in a vacuum chamber. The Linman '249 apparatus and the present inventors' apparatus are nominally similar to the known hand vacuum pump, with the constriction ring replaced by a pneumatic constriction cuff, providing a range of cuff pressures, to constrict venous blood flow to any degree.

Linman '249 is silent as to evidence, either theoretical or clinical, that the condition of the dilated and relaxed arteries and veins is any different after treatment than before treatment. Linman '249 is silent regarding his vessel distensions and relaxations to produce a beneficial outcome for the patient after treatment. That is unlike the present inventors, who have shown that dilation of arteries and veins immediately and temporarily increases vessel elasticities, causing an immediate and temporary reduction in heart workload, which causes an immediate and temporary increase in blood flow everywhere in the body.

The present inventors have also shown, in accordance with their invention, that periodic dilation and relaxation of arteries and veins gradually increases the elasticities of these vessels, so that heart workload is gradually reduced and blood flow throughout the body is gradually increased.

Blood flow measurements, made with the FPW device for the procedure of the present inventors, can be compared with flow measurements for EECP. Maximum blood flow, using the vacuum apparatus, may be greater than the EECP maximum flow because arterial and venous pressures can be adjusted to obtain maximum vessel elasticities, corresponding to maximum blood flow throughout the body.

Five (5) medical applications of our inventive apparatus follow. One application is the additional advantage of our passive air-vacuum exerciser. In the vacuum mode of passive exercise the periodically dilated arteries and veins exercise surrounding muscle. For patients and others who use the passive vacuum-air exerciser regularly, the periodic use will gradually increase the elasticities of arteries and veins, to increase whole body blood flow to treat existing conditions and may prevent or slow the progression of other conditions. For those patients who use the vacuum-air exerciser regularly (periodically), their whole body blood flow will gradually increase to a higher level so that, in case of a heart attack or stroke, they already have a higher level of blood flow into the heart and brain, which may benefit the injured heart or brain.

The basic air and vacuum pressure system described herein is cost effective because it has several medical applications: (1) Noninvasively increasing the elasticities of arteries and veins in arms, legs, hands, and feet to increase whole body blood flow to treat many medical conditions; (2) Use of the noninvasive method to increase elasticities of arteries and veins in combination with noninvasive vacuum angioplasty to attain greater whole body blood flow thereby than using either method separately; (3) Air and vacuum pressure apparatus to apply, alternately, periodic air and vacuum pressures to arms, legs, hands and feet to exercise muscles from the outside (air pressure) and from the inside (vacuum pressure to dilate arteries and veins to exercise surrounding muscle); (4) The vacuum pressure mode of the exercise apparatus periodically dilates the arteries and veins to increase elasticities, to increase whole body blood flow, an additional advantage of vacuum pressure exercising; (5) Patients who regularly use this air-vacuum exerciser will increase their level of whole body blood flow so that, in case of a heart attack or stroke, the heart, brain and the entire body already has a greater level of blood flow into the heart and brain and everywhere else, which may benefit the injured heart or brain.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. A method for passive physical exercise of a patient, the method being for exercising to gradually increase the elasticity of arteries, veins and adjacent muscles of a portion of a patient's body located in a vacuum chamber remote from the heart, to gradually reduce heart workload, to gradually increase whole body blood flow, to gradually provide more oxygen and nutrients to the cells of the whole body, to gradually increase a rate of removal of cell waste products, to treat a patient's diseases and conditions throughout the body, to prevent or slow the progression of diseases and conditions throughout the body and to provide other passive exercise benefits throughout the body, the method consisting essentially of:

a) providing a vacuum chamber, the vacuum chamber being configured for receiving a portion of a patient's body that is remote from the heart, the chamber being depressurizable;
   b) providing a vacuum source, the vacuum source being configured for inducing a negative pressure in the vacuum chamber;
   c) locating a portion of a patient's body remote from the heart in the vacuum chamber;
   d) causing the vacuum source to induce a negative pressure on the portion of the patient's body remote from the patient's heart;
   e) causing the vacuum source to relieve the negative pressure to return the pressure in the vacuum chamber to ambient pressure after a predetermined period of time;
   f) inducing and relieving the negative pressure a sufficient number of times to provide passive physical exercise and gradually increase the elasticity of the arteries, veins, and adjacent muscles of the portion of the patient's body remote from the heart located in the vacuum chamber, to gradually reduce heart workload, to gradually increase whole body blood flow, to gradually provide more oxygen and nutrients to the cells of the whole body, to gradually increase the rate of removal of cell waste products, to treat the patient's diseases and conditions throughout the body, to prevent or slow the progression of diseases and conditions throughout the body and to provide other passive exercise benefits throughout the patient's body; and
   g) inducing and relieving the negative pressure independent of the patient's heartbeat.

2. A method for passive physical exercise of a patient, the method being for exercising to gradually increase the elasticity of arteries, veins and adjacent muscles of a portion of a patient's body located in an air pressure chamber remote from the heart, to gradually reduce heart workload, to gradually increase whole body blood flow, to gradually provide more oxygen and nutrients to the cells of the whole body, to gradually increase the rate of removal of cell waste products, to treat a patient's diseases and conditions throughout the body, to prevent or slow the progression of diseases and conditions throughout the body and provide other passive exercise benefits throughout the body, the method consisting essentially of:

a) providing a chamber, the chamber being configured for receiving a portion of a patient's body that is remote from the heart, the chamber being pressurizable;
   b) providing an air pressure source, the air pressure source being configured for inducing a positive pressure in the chamber;
   c) locating a portion of a patient's body remote from the heart in the chamber;
   d) causing the air pressure source to induce a positive pressure on the portion of the patient's body remote from the patient's heart;
   e) causing the air pressure source to relieve the positive pressure to return the pressure in the chamber to ambient pressure after a predetermined period of time;
   f) inducing and relieving the positive pressure a sufficient number of times to provide passive physical exercise and gradually increase the elasticity of the arteries, veins, and adjacent muscles of the portion of the patient's body remote from the heart located in the air chamber, to gradually reduce heart workload, to gradually increase whole body blood flow, to gradually provide more oxygen and nutrients to the cells of the whole body, to gradually increase the rate of removal of cell waste products, to treat the patient's diseases and conditions throughout the body, to prevent or slow the progression of diseases and conditions throughout the body and to provide other passive exercise benefits throughout the patient's body; and
   g) inducing and relieving the positive pressure independent of the patient's heartbeat.

* * * * *